United States Patent [19]
Cosman

[11] Patent Number: 5,778,043
[45] Date of Patent: Jul. 7, 1998

[54] RADIATION BEAM CONTROL SYSTEM

[76] Inventor: Eric R. Cosman, 872 Concord Ave., Belmont, Mass. 02178

[21] Appl. No.: 718,288

[22] Filed: Sep. 20, 1996

[51] Int. Cl.$^6$ ............................................. A61N 5/10
[52] U.S. Cl. ............................................. 378/65; 378/206
[58] Field of Search ....................................... 378/65, 206

[56] References Cited

U.S. PATENT DOCUMENTS 5,553,112  9/1996  Hardy et al. ........................... 378/65

*Primary Examiner*—Craig E. Church
*Attorney, Agent, or Firm*—Darby & Darby, P.C.

[57] ABSTRACT

For quality assurance of radiation beams from a radiation source used for therapy of a patient, a reference structure is attached to the patient on the radiation therapy machine in a known position relative to the patient and the radiation machine. Predicted projection contours of the radiation beams onto the reference structure are determined and described on the reference structure. Field lights in the radiation machine through the collimator aperture of the beams are cast upon the reference structure and the associated light contours of the beam apertures are compared to the described or predicted contours from treatment planning or from quality assurance set up. Several forms of such beam quality control system and methods accommodate the specific objectives. Computer-generated beams projection sheets are overlaid on the reference structure corresponding to predicted field light projections.

10 Claims, 6 Drawing Sheets

RADIATION BEAM CONTROL SYSTEM

BACKGROUND AND SUMMARY OF THE INVENTION

The use of sterotactic method for irradiation of patients for treatment of cancer and other diseases is now well known and makes use of radiation sources such as linear accelerators (LINACs) for X-rays, cyclotrons for heavy particles, cobalt machines for gamma radiation. The stereotactic radiosurgery and stereotactic radiotherapy methods for use on LINACs is exemplified by the XKnife System of Radionics, Inc. (Burlington, Mass.). With this system, a stereotactic reference frame such as a head ring is fixed to the patient's body and a graphic reference device such as a rod and diagonal structure is attached to the head ring. CT or MR data of the patient's head with the graphic reference structure in place provides the image data involving the anatomy as well as fiducial markers in the slice views to enable a transformation or mapping of the data from the coordinate system of the CT or MRI scanner to the stereotactic coordinate system of the head ring with its graphic reference structure attached. This technique is well known from the use of stereotaxy over the last twenty years (see, for example, the BRW/CRW Stereotactic Systems of Radionics, Inc.). The CT data for radiosurgery is imported to a computer processor which enables dose treatment planning for targets such as tumors to be developed. The result is a treatment plan for X-ray beams from the LINAC to focus on the target volume for therapy. At the time of irradiation, the patient, with the head ring still in place, is moved to the LINAC machine and is attached to the LINAC couch, typically via the head ring. A stereotactic reference frame is again attached to the head ring, which enables alignment of the planned target from the treatment planning computer program to be positioned at the so-called isocenter of the LINAC. The isocenter is the point where all the radiation beams converge from all the angular degrees of freedom possible with the X-ray beam LINAC. The X-ray beams of a LINAC, for instance, can be brought in in a nearly full angular range governed by the rotation angle of the patient couch and the rotation angle of the gantry of the beam delivery of the LINAC. This technology is fully described in the brochures on the XKnife System by Radionics, Inc. and in the literature on LINACs (for example, manufactured by Varian, Siemens, and Philips medical companies).

The sterotactic treatment planning computer enables the clinician to define the target volume (such as a tumor) and many other normal anatomical structures around it. The plan of the X-ray beams from the LINAC can also be calculated using graphic computer algorithms and dose algorithms so that a complete dosimetry plan in three dimensions can be developed by such stereotactic LINAC treatment planning computer and software systems. An example of this is the XKnife radiosurgery software from Radionics, Inc. All of the import beams, or ports, from the LINAC can be pre-planned. In some cases, these beams have a circular profile, but in other cases they are irregular, depending on the therapy and dose description desired. The beam profile is defined by high mass collimator structures which may have conical, circular bores (circular collimators) or irregular shapes (such as so-called cut-block collimators). Circular collimators and cut-block collimators are well known in the radiation therapy literature. A variety of beam (port) angles can be achieved by the couch and gantry angular degrees of freedom on the LINAC mentioned above. In this way, the angular input of the ports as a computed from the treatment planning software can be implemented physically by angling the collimators to these appropriate angles relative to the patient by rotation of the patient couch and the LINAC gantry. All this is done in a coordinate reference frame relative to the patient's head ring, and thus the beam angles and target position, as well as target position and target volume, are defined in the so-called stereotactic coordinate system referenced to the patient's head ring and thus referenced to the CT or MR image data described above.

The target position defined from the treatment planning system can be moved to the isocenter of the X-ray beams of the LINAC by means of laser lights mounted in the LINAC target room .this can be done stereotactically by attaching a reference frame on the patient's head ring which has coordinate settings in the stereotactic coordinate system which can be set to the target position. The laser lights from the lateral, frontal, and top position can be played upon such a settable reference frame so that the patient, and therefore the target volume, can be moved to the LINAC isocenter. This technique of laser alignment and moving the patient's body on the LINAC couch so that the preplanned target volume stands at the LINAC isocenter is well known in the current literature.

Various stereotactic reference frames have been used with linear accelerators for aligning a target volume that has been preplanned stereotactically by a treatment planning computer to the isocenter of the linear accelerator beams. For example, the laser target localizer frame of the XKnife System from Radionics, Inc. involves a set of cross-hairs that can be moved to the stereotactic target coordinates onto which pre-aligned laser beams on the linear accelerator enable setting of the laser target localizer frame to isocenter. The localizer frame is attached to a patient's head ring, and therefore referenced with the sterotactic coordinate system associated with the CT scanner. Another device for this purpose was reported by M. Brada, et al. and involves a plastic box-like structure which can be attached similarly to a patient head ring. The orthogonal projected position of stereotactic target coordinates for the target are marked on the side plates of the plastic box, and these markers are then aligned to the LINAC laser lights in a similar way. Marking sheets are used which can be prepared from computer outputs for the target coordinates and attached to the side plates of the reference box for this purpose.

A limitation of the procedure for confirming the X-ray ports as they are beamed to the patient's body from the LINAC to the target volume is that confirmation of these port geometries and positions are not readily available. The so-called "port film", which is the exposure of a photographic film by an X-ray beam from the LINAC through a given port or collimator can be done with or without the patient in place on the LINAC. This can be time-consuming, and is typically done only once. Patients, however, come back for multiple "fractions" or repeat episodes of radiation in the case of cancer treatment. Thus, a patient may come back as many as thirty times for repeat irradiation to exactly the same target, in exactly the same position, and with the same beam ports each time, spanning perhaps thirty days of fractionated radiation. The efficient use of LINAC time is important, and therefore a rapid and certain method of checking that for each fractionated irradiation the beam ports and beam shapes are correct according to the treatment plan is important as part of a quality assurance procedure. It must not take a large amount of time by the radiation technologist. Such verification of beams for stereotactic radiosurgery (which is a single, high dose irradiation of a tumor in one session, typically with multiple beam arcs of the X-ray beam over the patient's body) and stereotactic radiotherapy (meaning typically multiple fractionated stereotactic doses of beams to the target) is not presently radially available. The consequence of mis-irradiating a patient can be disastrous, even fatal. The use of conformal cut-block collimators complicates the problem even further since irregular shapes at compound oblique angles to the patient will be used. It is desired, therefore, to have a method whereby such circular or irregular-shaped beam ports can be checked at the particular gantry and couch angle appropriate for the radiation treatment plan developed.

In general, the system and method of the present invention is directed at an improved system for accomplishing the quality assurance of radiation beams, ports, and target positions as set up on radiation delivery machines such as those mentioned above. The system offers a capability of quickly and certainly confirming a direction, shape, and orientation of beams from multiple directions aimed towards the patient's body and towards a predetermined target volume within the body. This is done in stereotactic space, meaning that the confirmation is done relative to the treatment plan developed from a CT or MRI scan data set with reference to either a graphic reference structure, graphic fiducial means, or other stereotactic structures applied on or in the patient's body. In disclosed embodiments, for example, the projected profile of multiple beam ports can be visualized on a template located near the patient's body which has been determined from the treatment plan computer and positioned stereotactically relative to the patient's body and the linear accelerator. In one embodiment, a light source projecting through the collimator is played upon a computer-generated target sheet which has a preplanned profile of the X-ray beam projected through the collimator and directed towards the body. Light projection is seen to conform to the predetermined X-ray projection giving a simple and reliable method to check that a particular beam port is appropriate, and this check can be done repeatedly. A stereotactic reference frame to be attached to the patient's body or on the LINAC couch and referenced to the patient's body according to the stereotactic coordinate system from the CT scan data is disclosed in one embodiment and computer generated target sheets from the treatment planning computer are attached to this reference frame for the purpose of beam port projection confirmation via field lights or port film shots.

A process is disclosed herein which involves CT or MR scanning of the patient with graphic reference structures in place to produce computer data to develop a treatment plan and a plan of beam ports as well as to develop target and port output does that can be applied to a LINAC reference structure at the time of irradiation for the purpose of checking that the correct beam port and port angles have been used. Specific embodiments of the system for checking visually by port films or LINAC field light projections are described.

BRIEF DESCRIPTION OF THE DRAWINGS

In the drawings, which constitute a part of the specification, exemplary embodiments exhibiting various objectives and features hereof are set forth, specifically.

DESCRIPTION OF THE INVENTION

Figure 1:
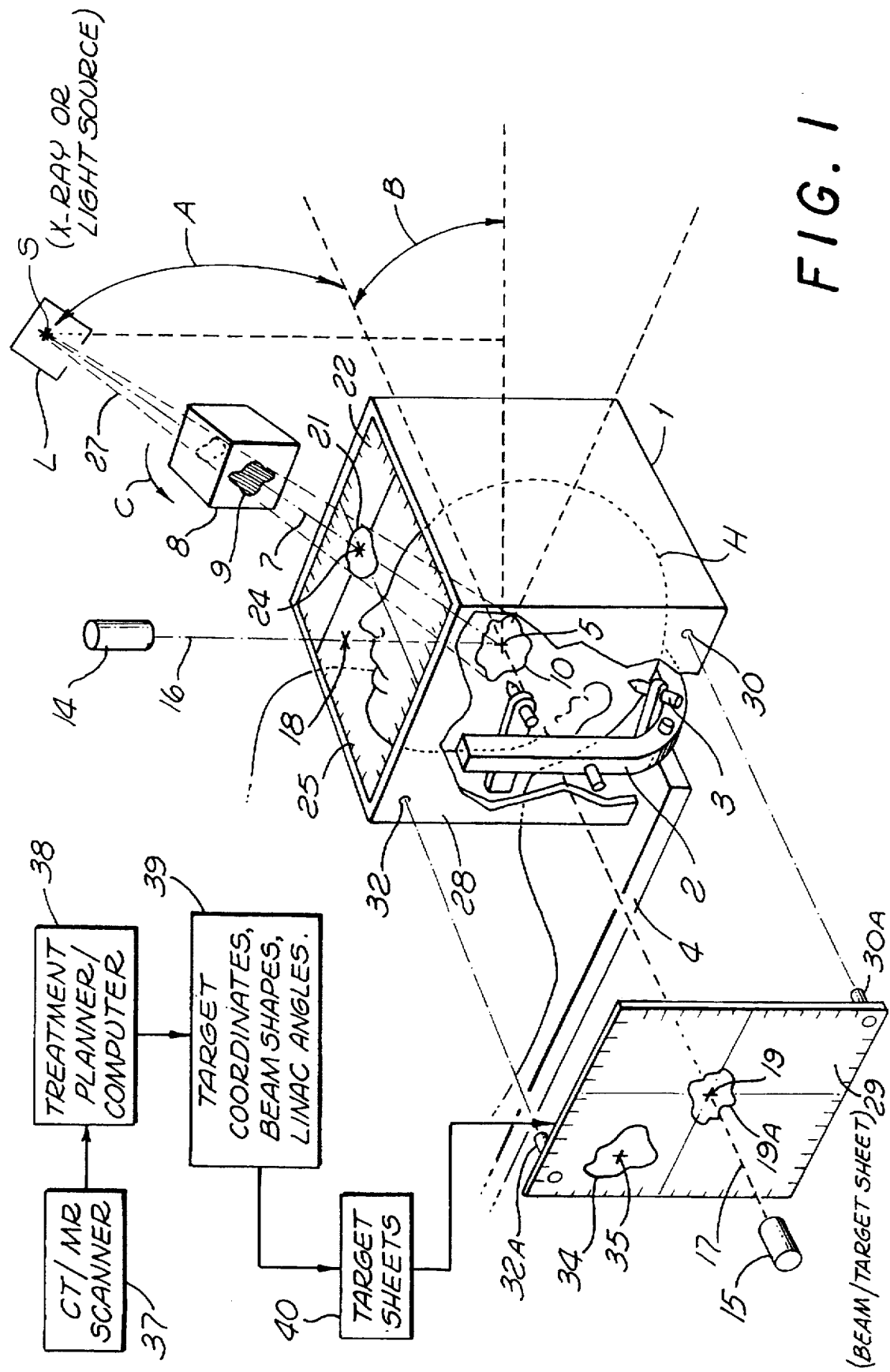
FIG. 1 is a schematic diagram of a system constructed in accordance with the present invention involving a stereotactic head ring and stereotactic reference frame.

The following embodiments illustrate and exemplify the present invention and concepts thereof, yet in that regard, they are deemed to afford the best embodiments for the purpose of disclosure and to provide a basis for the claims herein which define the scope of the present invention. Referring to FIG. 1, an illustration of a stereotactic LINAC reference structure is shown attached to the patient's head H. It comprises a box or frame structure 1 that is fixed to a head ring 2 which is securely attached to the patient's head H by head screw anchors 3 in multiple positions around the head. This is a standard type of stereotactic attachment (see Radionics, Inc. instrumentation). The patient H is lying on the LINAC couch 4, and such couches are capable of translating the patient's position until a predetermined target point 5 in side the patient's head stands at the isocenter of the linear accelerator. The LINAC is schematically illustrated by apparatus element 6, and it has a source S within it of X-rays. Also within it is a source of visible light referred to as the field lights, which shine typically in the same direction as the X-ray out of the gantry of the LINAC. Depending on the couch angle and the gantry angle of the LINAC, the direction of a beam port, illustrated by the line 7, may correspond two angular degrees of freedom shown as A and B, A being the gantry angle and B being the couch angle. Attached to the so-called head of the LINAC on the gantry is a collimator 8, which in this case has an irregular-shaped opening 9 to allow the X radiation from the source S to emerge from the LINAC towards the patient H. The block 8 may be made of lead, or some head material which isopaque to X-ray except for the aperture 9 through it. The aperture 9 may have a particular shape which has been predetermined and cut according to the treatment planning computer which has determined the dose plan for the target region. For example, it is common that an irregular target volume such as a tumor, indicated by 10, in the patient's body may require several input beams, and thus collimator positions 7, to be beamed into the patient to accumulate a high dose of radiation over the target volume 10 while spreading the radiation to normal tissue around it to acceptable levels. This is the convergent beam stereotactic method. In such situations, a variety of cut collimators 8 (referred to as cut blocks) and couch and gantry angles, or port angle 7, would be required for multiple conformal and convergent sterotactic irradiation. The isocenter 5 of the LINAC L is located at the convergence of all the X-ray beams corresponding to the center of rotation of the gantry and couch angles, i.e. A and B. This is specified by laser beams from wall-mounted lasers such as 14 and 15 which direct laser beams 16 and 17 in a calibrated way to the intersection point 5, which is isocenter. Thus, by moving the patient H with the target structure 1 attached so that the laser beams intercept the calibrated positions marked on the reference box, such as marked crosses 18 and 19, will enable that the preplanned target volume 10, as seen in the CT image in stereotactic space, can be positioned at the isocenter point 5 of the X-ray beams. The treatment planning computer will also specify the port parameters such as the gantry and couch angles A and B, respectively, and the shape of the port 9 and its angular orientation, illustrated by the collimator rotation angle C, which is also typical for linear accelerators. In accordance herewith, a contour 21 is described on the surface 22 of one of the faces of the reference frame 1 to correspond to the correct and preplanned projection of the port shape 9 when it is directed at the correct angles A, B, and C at the target volume 10. Such a contoured 21 can be computed by the treatment planning computer. The treatment planning computer has stored in it the CT/MR image data that has been referenced stereotactically to the stereotactic head frame 2 and thus to the reference structure 1 prior to placement of the patient on the LINAC. Thus, the position of the projection of the appropriate port direction 7 and the shape of the port 9 can be described by the contour 21 and calculated in the treatment planning computer 23. We note also that a line can typically be drawn between the source point and the isocenter 5. This line will have an intersection on the structure surface 22 at a point indicated by the cross 24. This can also be marked on the surface 22. It may also be that the upper surface may also have scale lines 25 which correspond to a coordinate system associated with the reference structure which may be the stereotactic coordinate system associated with the head ring during the CT and MR scanning and transformation to the head ring coordinate space.

Before the X-ray source S is turned on, a field lamp source at the same position may also be turned on and the projection of the field lamp light rays 27 follow the same path approximately as the X-rays when the X-ray machine is turned on. Thus the cone of rays 27 that project through the aperture opening 9 will also be cast upon the upper surface 22. If they match the calculated and marked perimeter 21 on the surface 22, then this is a physical and visible confirmation that the port direction 7, port shape 9, and LINAC angles A, B, and C are all in accordance with the treatment plan. Thus, the observation that the field lamp projection from source S through the collimator prior to X-ray beam is made by this reference box with field projected contour 21.

Each side of the reference frame 1 may need beam contours such as contour 21 cited above on it if beam ports directed toward the target 10 pass through those sides of the reference structure. Thus, for example, on another side 28 of the reference structure, a target sheet 29 may be installed on reference pins 30 and 32 by pins 30A and 32B. Target sheet 29 may have a cross position 19 associated with the isocenter projection along the Cartesian axis of the linear accelerator as also referenced by the laser beam 17. There may be another contour 34 with central beam projection 35 printed or drawn on the target sheet 29 to indicate the projected view of another beam port from a direction different from that of beam 7 which may be required from the treatment plan. The shape of the contour 34 again is in accordance with the oblique projection of the collimator aperture from that direction. Such beam target sheets as 29 can be prepared based on the treatment planning computer and for a given patient and treatment plan. They may be secured to each side of a reference frame structure such as 1 at the time of irradiation. The center of the target structure 10 may be positioned at the isocenter 5 by moving the patient on the LINAC couch such that the laser beams 16 and 17 are in coincidence with the reference points 18 and 19, as marked on the target sheets. This is in accordance with prior practice. In addition, the target sheets may contain one or more contour lines such as 21 and 34 together with the principal beam axis points such as 24 and 35 to specify the projections of the various and multiple beam ports to be delivered. They may also contain projected contours of the target volume 10 along the line 17 as shown by contour 19A.

At the time of patient preparation on the LINAC, a beam port such as 7 can be set up and a collimator 8 installed on the gantry of the LINAC. The patient may be moved to the target position associated with isocenter 5. The field lamps S in the linear accelerator are turned on and the light from them shines through the collimator aperture 9 to be cast upon the surface 22. The observation that that field lamp projection through the collimator coincides with the shape, position, and orientation of the preplanned, reconstructed, projected line 21 on the surface on the treatment planning computer confirms that port position and that the correct cut-block collimator is in place. At this point, the reference structure 1 may be removed from the head ring 2, and the X-ray irradiation from the source X may be turned on for the appropriate amount according to the treatment plan. At that point, the reference frame 1 is put back onto the head frame, and a second port can be similarly checked and irradiation delivered. This sequence can continue through multiple ports. It is also true that arc sweeps of collimators such as is commonly done with circular collimators can be qualified in the same way by such target sheets with beam projections described on them. For example, the projection of a circular collimator instead of an irregular collimator shape such as 9 as it sweeps across the reference structure 1 would describe a pass of light. Thus a contour path from the treatment planning computer can be described on the surface of the box and confirmed by field lights from the source S.

The target sheet 29 can be prepared automatically by the computer for a given patient and treatment plan. For example, these target sheets may be made from paper that can be printed upon by a computer-controlled printer such as a laser printer from the treatment planning computer. The resulting target sheets can be indexed according to the position on the reference structure 1 and they can be fixed to the appropriate side in the correct position by index markers, or pins, or other reference means. Thus the computer can generate the target sheets directly and thus the subjectivity of human drawing of such contours can be avoided. This is illustrated by the block diagrams 37 indicating the CT scanner acquisition of image data being downloaded into the treatment planning computer 38 in the target coordinates, beam shapes, and LINAC angles 39 are generated and a computer output 40 of the target sheets such as sheet 29 are prescribed. Alternatively, manual tabular outputs of the LINAC parameters 39 can be given and the contours such as 34 can be manually described on target sheets 29 or directly on the faces or surfaces of the reference structure 1.

With regard to calculation of projected contour 21, given an aperture shape 9 and LINAC angles A and B, this is a matter of projected geometry and ray tracing. The contour 7 is closely related to the so-called "beam's -eye view" of the target volume 10. The beam's eye view is used, for example, in the XKnife Radiosurgery System (Radionics, Inc., Burlington, Mass.) to display a two-dimensional picture, the view from the direction 7 of the target volume 10. This will give rise to a perimeter for the target volume 10, as seen by point source S. The perimeter is a set of rays corresponding to the outer extremities of the beam's-eye view projecting back to the source S. The equation for the surface 22 can be described as a plane in the stereotactic reference frame or the localizer 1. Each of lines from the source S (assumed to be point-like here for the sake of example) through the perimeter of the predetermined collimator 9 will intersect the surface 21 at a unique point. The intersection of the locus of points corresponding to these interception points of the cast lines through collimator 9 will be the contour 21. Computational techniques for the intersection of lines through surfaces is given in the book *Graphic Gems*, edited by A. S. Glassner, Academic Press Professional, 1990. Once the target volume 10 has been defined by the dose planner, based on radiation and anatomical considerations which are common in radiotherapy treatment planning, the mathematical contour for the collimator 9 can be determined by the projection of the beam's-eye view back to the source S. Once this contour has been determined, the forward projection onto the surface 22 can be calculated in the computer, as described above. If the surface 22 is not a plane but rather a curvilinear surface of known geometry in the stereotactic coordinate space in the localizer 1, a similar locus of intersection lines of the rays from the source of through the collimator can be determined, thus defining the contour to be described on the curvilinear surface analogous to 22. This can be computed in the treatment planning computer 38, and overlay sheets, graphs, templates, or output data can be thereby derived for the practitioner and transcribed to the surface 22 or analogous curvilinear surface.

Figure 2:
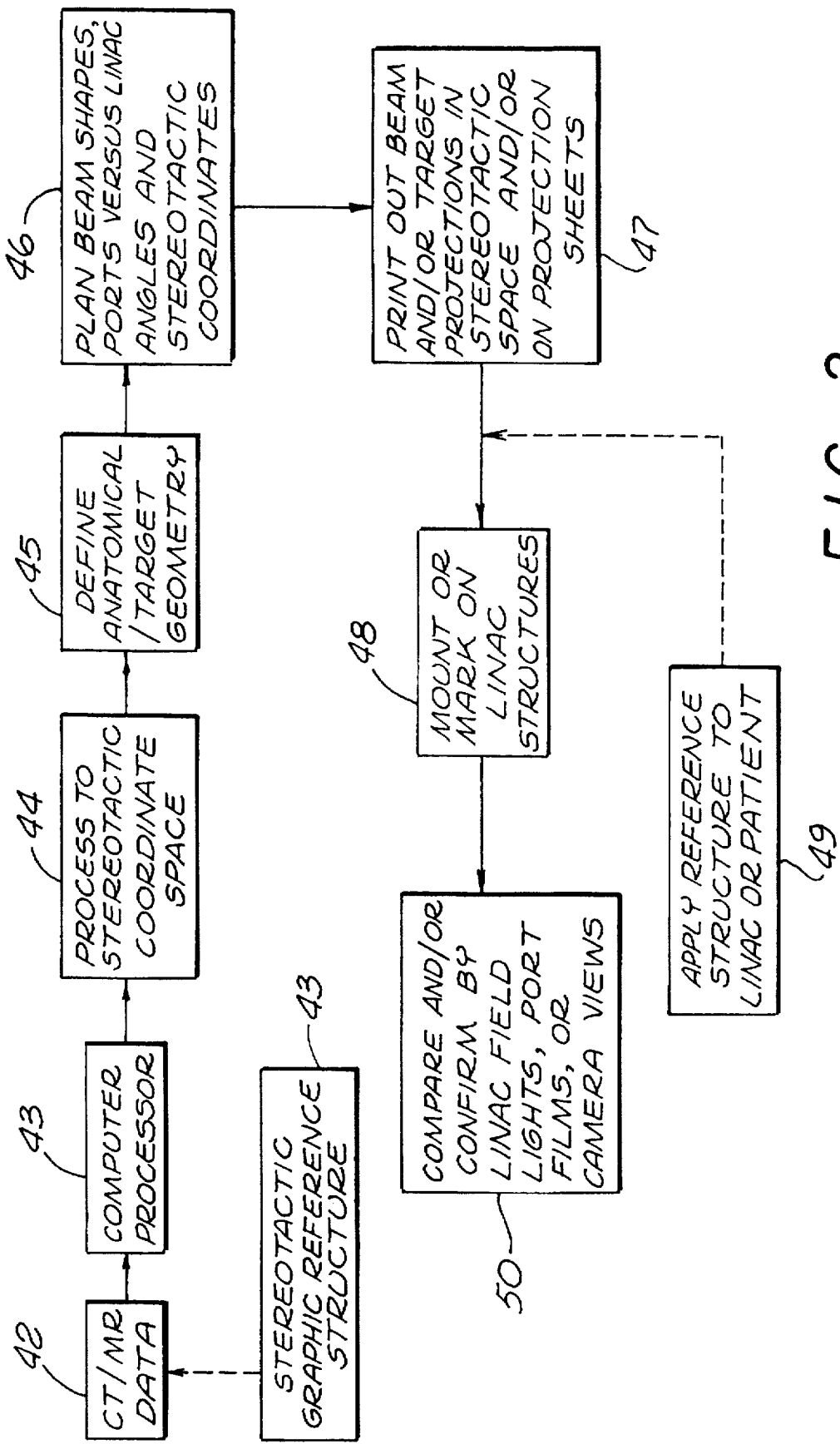
FIG. 2 is a schematic diagram showing the steps in accordance with the present invention of checking stereotactic beam ports.

The process in accordance herein is described in one embodiment in FIG. 2. CT scan data 42 is acquired typically with the application of a stereotactic graphics reference structure 43 secured to the patient's body. Such a reference structure 43 is illustrated by the rod and diagonal localizer frame attached to the stereotactic head ring in the BRW stereotactic System of Radionics, Inc. Burlington, Mass. The CT data including stereotactic reference indicia, is processed in the treatment planning computer 43 which transforms or maps the CT data or MR scanner data into the stereotactic coordinate system of the graphic reference structure 43 by means, for example, of a computer software program or the graphical method (see Radionics literature on the BRW and CRW Stereotactic Systems). Furthermore, software and user interface 45 may allow contouring and definition of anatomical targets, shapes, positions, and pathologies such as tumors. This in turn enables a treatment plan for dosimetry of the target volume, avoiding critical structures, to be developed with appropriate planning software 46. Such a plan gives rise to port angles, LINAC angles, port shapes, etc., all prescribed in the stereotactic coordinate system of, for example, the stereotactic reference structure 43 (this is illustrated by XKnife Radiosurgery System of Radionics, Inc.). Thereafter the computer processor 43 can print out the information on beam ports and LINAC data in the form of tables, or target sheets, or overlay sheets 47. These can be mounted by a registration process 48, such as illustrated in FIG. 1 above, to a reference structure 49 similar to the reference box 1 in FIG. 1. At this point, the patient can be appropriately moved so that the selected target volume can be placed at LINAC isocenter, and the field lights of the LINAC turned on to confirm that a chosen collimator and LINAC angles are appropriate as checked by the projection of the field lights onto the projection or target sheets. The step of comparison 50 may also include doing actual X-ray projections through the collimator with an X-ray sensitive film on the opposite side of the reference structure 1 to confirm the X-ray projection of the collimator (see below).

Figure 3:
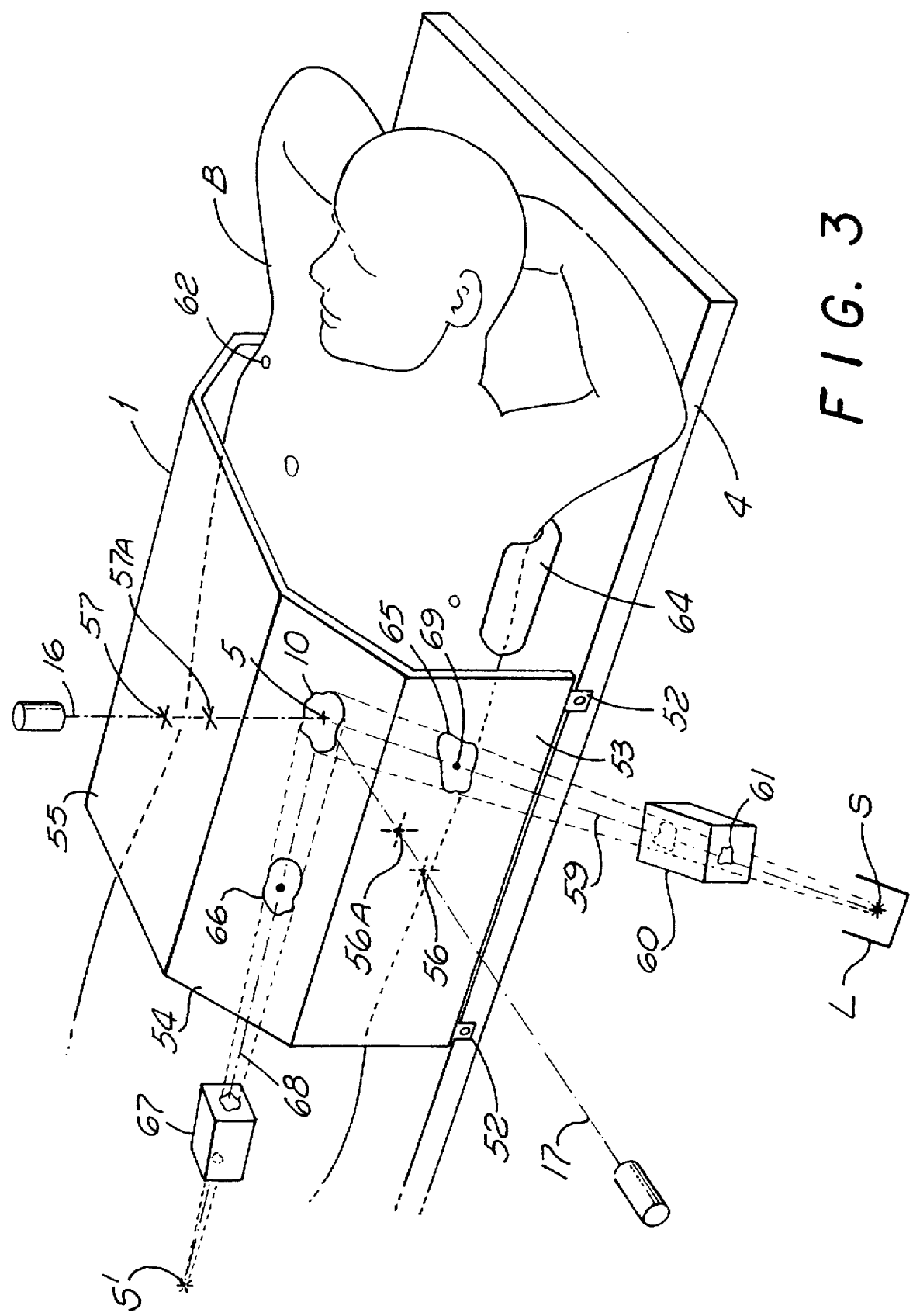
FIG. 3 is a schematic diagram of an alternative embodiment in accordance with the present invention.

Referring to FIG. 3, a patient's body A is placed on a radiation couch 4, and a reference structure 1 is coupled to the couch 4 by location elements 52. On the surfaces 53, 54, and 55 of the structure 1, there may be markings 56 and 57 corresponding to the position of isocenter 5 on the cardinal axes 17, 16, respectively associated with target volume 10 similar members in this figure refer to similar numbers in the figures above). A tattoo marking 56A and 57A may be made on the surface of the patient's skin so that a rough check of the alignment of the laser beams to the actual patient's anatomy may be done. This may enable the proper registration of the patient's body B relative to the reference structure 1 so that it is positioned correctly in stereotactic space of the reference structure 1. In addition, a port direction angle 59 is shown with a port block 60 and aperture 61. The angular orientation of central ray 59 can be specified, for example, by the LINAC couch and gantry angle relative to the patient's body B and the reference frame 1. Thus the direction 59 is a stereotactic direction with reference to these LINAC angles and also therefore with reference to the reference frame 1. In the case of body stereotaxy, the image scan data from the scanner could have been indexed to the patient's body by index markings 62, and this constitutes the frameless technique of stereotactic transformation as described in, for example, the paper of Guthrie and Adler on frameless stereotaxy. It is also true that the patient's body B maybe positioned relative to the table 4 by a conformal contour structure 64 which is shaped to the patient's body B and anchored to the couch 4. On the surface 53 is described a contour 65 corresponding to the calculated projection of port aperture 62 along ray 59 by the treatment planning computer. The field lights from source S in the LINAC, schematically indicated as L, approximate the predetermined line 65. This is a direct confirmation of the correctness of the port direction and collimator shape. A similar projection on surface 4 is indicated by the contour 66 corresponding to collimator 67 and a different port direction 68. The surfaces of such a body reference frame may have the projected beam contours on the surface for such a port qualification check.

The reference structure 1 may take many forms and variations. It may be a curved surface, domed surface, or cylindrical surface. It may have a frosted surface so that a technologist can write on it the patient's name and also graphically write on the contour lines, as described above. The surfaces may be flat to accept paper or printer readouts from the treatment planning computer that can be stuck or taped on directly with proper registration to these surfaces. The contour lines 65 may be made in ink, pencil, or crayon, but they may also be traced out by a radiopaque material such as a lead write to the appropriate wire. A lead wire can be fitted easily over a line on the surface and taped down. Thus, an X-ray test shot from source S through the port 61 to a film on the opposite side of the patient that is typically done in radiation therapy will confirm that the shape of the lea wire 65 corresponds essentially to the shape of the projected aperture 61. In addition, a radiopaque marker or simple ink marker 69 maybe placed on the central ray 59 for a given port. It is radiopaque, a port film, as described above, will show the aperture contour for the radiopaque block 60 on the X-ray film and, standing at the appropriate point, will be a radiopaque dot or cross corresponding to marker 69. Thus, port films as well as field lamp confirmation using such a reference structure is useful in checking the beam quality position and shape of the beam.

Figure 4:
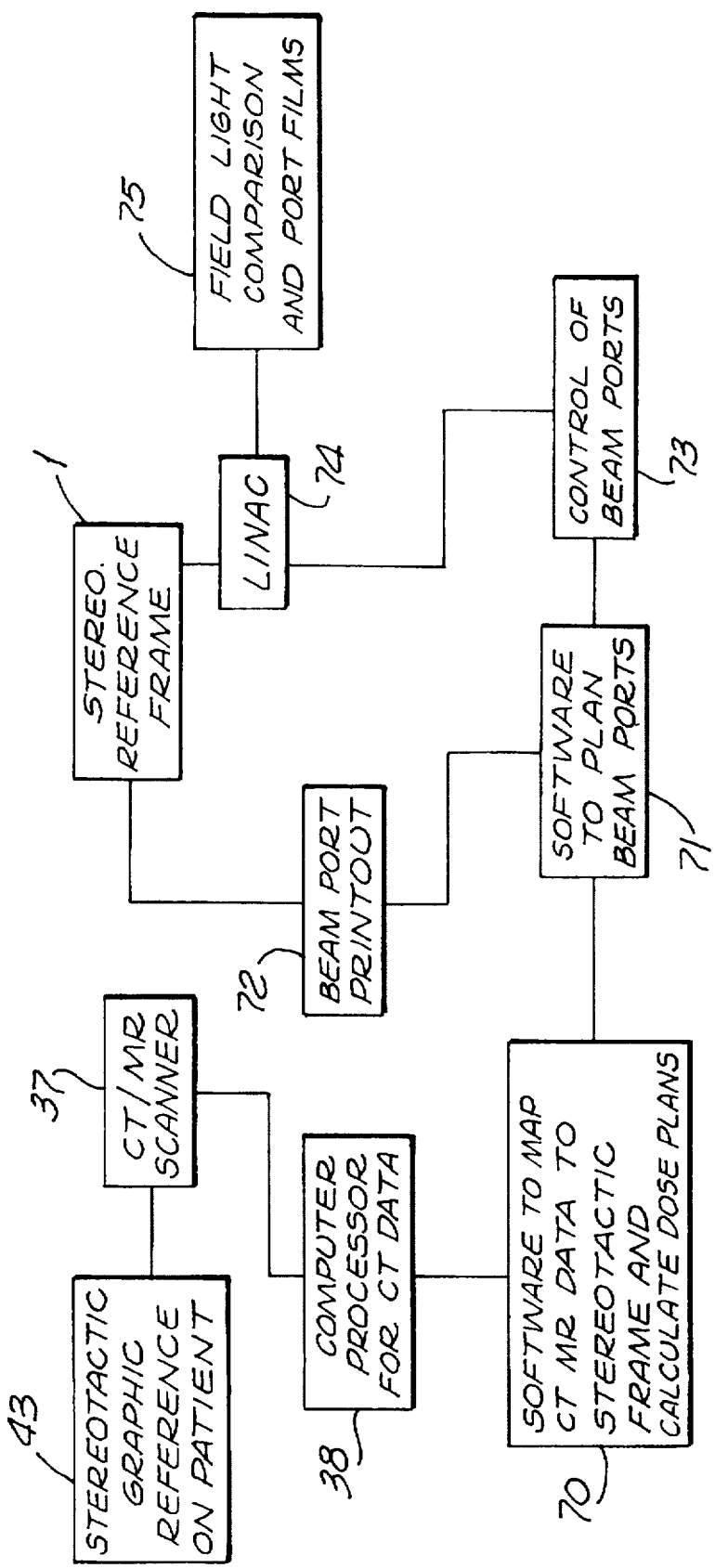
FIG. 4 shows a block diagram of a system in accordance with the present invention.

FIG. 4 illustrates a schematic system in accordance herein in which a stereotactic graphic reference structure 43 is attached to or near the patient during scanning by a CT scanner 37. A computer processor 38, perhaps for example in the form of a high level computer graphic workstation, assimilates the scan data from 37 and renders it graphically in three-dimensional or two-dimensional renderings such as exemplified by the XKnife System of Radionics, Inc. Software then transforms the scan data by its transformation software 70 into the stereotactic reference frame of 43. This is illustrated by the transformation process of Brown, U.S. Pat. No. 4,608,977. Treatment planning software 71 maybe used to optimize the beams and beam shapes to irradiate a desired tumor volume derived from the treatment planning software 70. The further software output processor 72 gives rise to printouts such as for the target sheets 29 in FIG. 1. Furthermore, beam ports planning software 71 can give rise to control parameters or data sets that can be used to cut collimator shapes or numerically-controlled cutting machines to cut heavy metal blocks (such machines as the Par Scientific device made in Denmark). Thus, software 70 can derive both port projection information as well as collimator manufacturing or processing information. Control 3 may, for example, be the control electronics for a multileaf collimator or mini multileaf collimator, as is manufactured by Varian, Siemens, Phillips, and other LINAC manufacturers. Control data from 73 may be coupled to the linear accelerator 74 so as to control the couch and gantry angles as well as collimator parameters. Also, the port printout 72 may be used to produce beam/target sheets that can be attached to a reference frame 1 attached to the LINAC couch or to the patient. Field light comparisons and film ports 75 can be carried out to demonstrate the correctness of the collimators with LINAC angles according to the treatment plan from software 70.

The systems enable quality assurance of simple or complex treatment planning with a radiation machine. It can check the correctness of cut blocks used on a LINAC to correspond to the correct couch gantry and collimator angles. It can be used simply and quickly by technologists since it is a sample visual check of a multi-parameter and three-dimensional situation.

As will be apparent by those skilled in the art, the system may take many forms with a multitude of variations. Various forms of the LINAC reference structure can be used. Various means of comparing the light, field, or port film to predicted shapes can be done. For example, vide/digital images of the light source or port films can be made, and these compared in the computer to the shapes corresponding to the calculated, projected views. Various means of printing out the target sheets with beam projections can be devised by those skilled in the art. For example, the treatment planning system can organize a particular port direction and reference frame side, printing out via a laser printer a sheet with appropriate indicia that can be taped on in the appropriate fashion to the reference structure. In view of these considerations, and as will be appreciated by persons skilled in the art, implementations and systems should be considered broadly and with reference to the claims set forth below.

Figure 5:
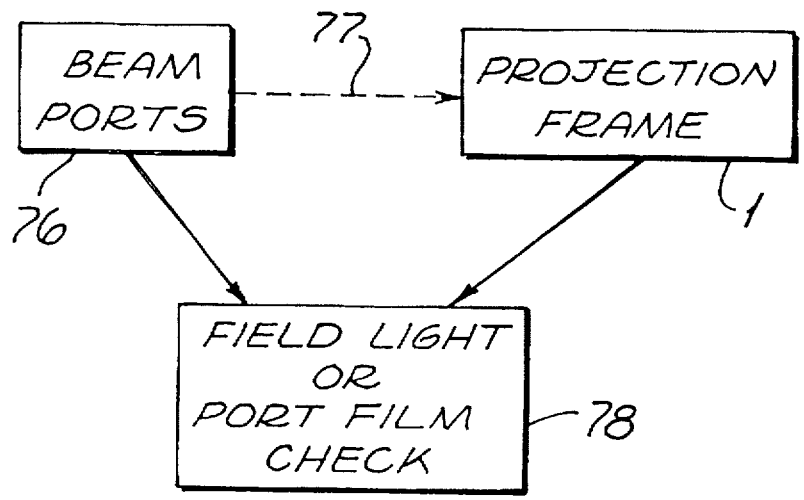
FIG. 5 shows a system diagram according to present invention.

FIG. 5 shows a schematic of a somewhat simplified embodiment of the present invention. Beam ports 76 may comprises a set of collimators having apertures to be directed in a specified direction towards a target within the patient's body. Beam ports and directions may be referenced to structure on the linear accelerator or a stereotactic coordinate system established relative to the LINAC, similar to the description above. A projection frame 1 is attached to the LINAC or to the patient on the LINAC, during initial quality assurance, the beam ports with projected field lamps through them may be used to establish the projection contours on the projection frame 1. This is indicated by the dashed line 77. For instance, a specific cut block representing a beam port may be set in a direction on the LINAC and field lamps turned on. The resulting light projection may shine upon the projection frame and the technician may thereby mark the frame with the projected outline of the beam port. This may be done for multiple ports at multiple directions. At a subsequent time, the patient and projection frame may be repeatedly attached to the LINAC, and the beam ports also attached to the LINAC. The initial markings of the projection frame 1 may then be used again to check the position of the beam ports with a field light check indicated by blocks 78. Furthermore, according to the description above, port films may also be used as a subsequent method or a substitution for field lights in this diagram.

Figure 6:
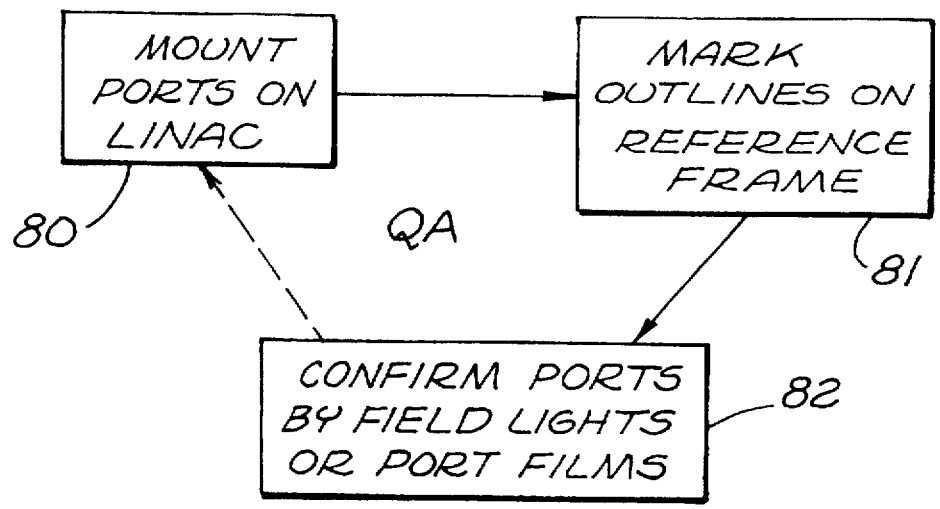
FIG. 6 shows a process flow diagram for the present invention.

FIG. 6 is a diagram illustrating this QA cycle. The beam ports or collimators are mounted onto the LINAC in step 80. The reference frame is marked by beam port projection outlines in step 81. The operator checks by field lights or port films the relationship of the projection of the beam ports so mounted with the outlines on the reference frame in step 82. If a confirmation or coincidence of the projection and outlines are confirmed, then the irradiation of the patient may proceed. If, however, there is a misalignment of the field light projections with respect to the reference lines on the reference frame, then a correction to the mounting of the ports on the LINAC or a check of the entire relationship of the reference frame to the LINAC may be made. This would be a practical quality assurance cycle in a standard radiation setting.

Figure 7:
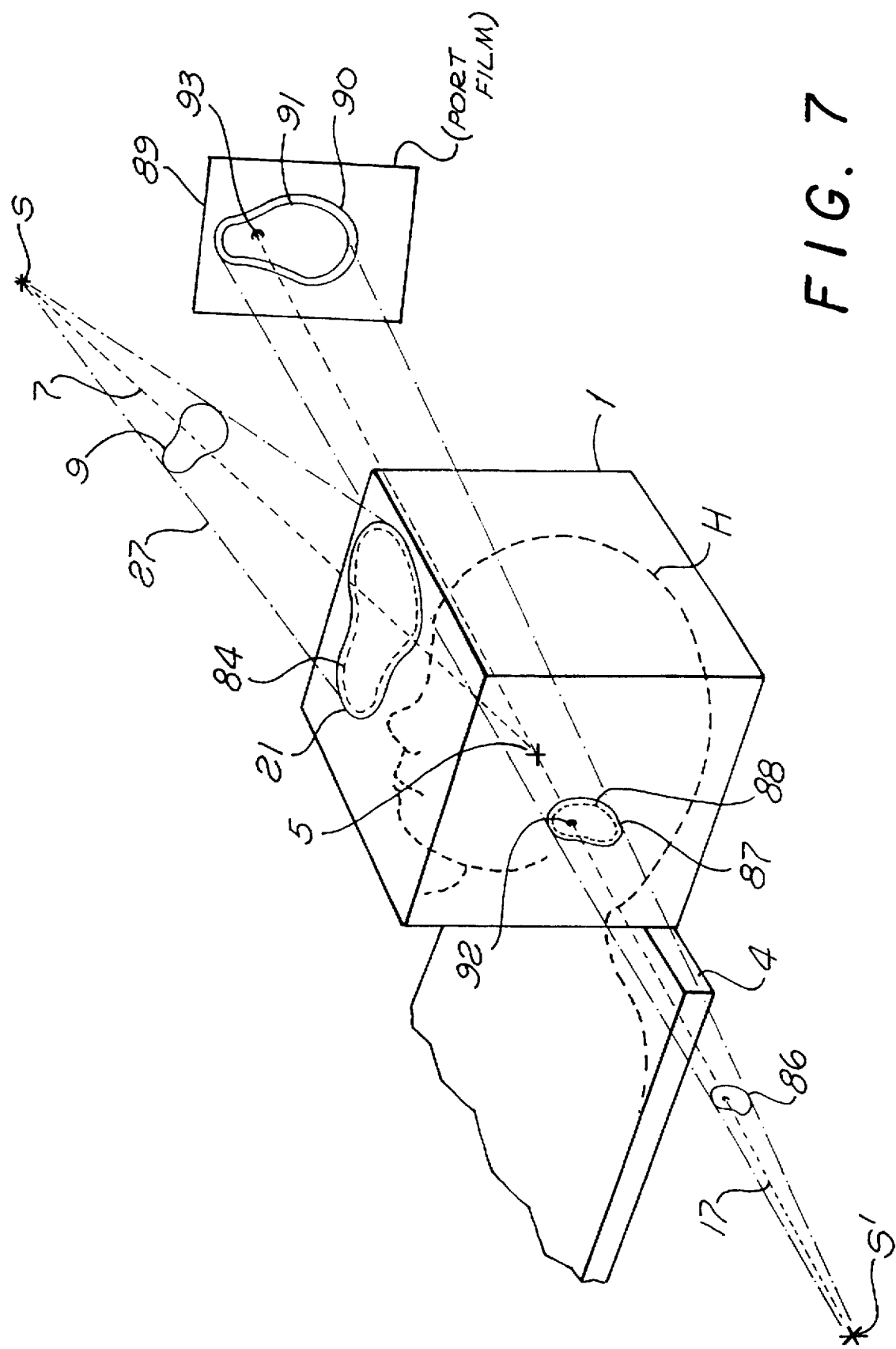
FIG. 7 shows a schematic diagram of a projection box with beam ports used in accordance with the present invention.

Referring to FIG. 7, a reference box 1 is attached to a radiation couch 4. A beam port is schematically indicated by element 9, and a light source or radiation source is indicated by S. The direction of the beam port is indicated by central lines 7, and the dashed lines 27 indicate the projection from source S through collimator 9. They intersect the reference box on the dashed line 84. The solid line 21 indicates a marking on the reference box 1 which is made, for example, by a technician who follows the contour of the projected dashed line 84 with a pen. Alternatively, as described above, contour 21 may be preplanned and printed out from a treatment planning system such as a computer printout. Thus, the placement of a beam port, such as 9 relative to a reference frame 1, can provide a method and apparatus to establish projection contours on the reference box. This may also provide a way of positioning the reference box 1 in the correct position relative to, for example, a LINAC isocenter point such as 5. For example, a laser source, light source, or X-ray source S' may be established along one of the cardinal Cartesian axes of the LINAC (this commonly done in LINAC suites). A port 86 may be established also coincident with that projected axis 17. A marking 87 on reference box 1 will correspond to correct alignment of reference box relative to cardinal axis 17. Thus, field lights from S' through collimator 86 will produce the projected dashed line 88, and if that is coincident properly from the contour line 87, a confirmation for one direction is made that reference box 1 is aligned to the cardinal axis 17 through an isocenter 5. Similar such confirmations for other ports on the cardinal axes can provide for complete alignment of reference blocks 1 relative to the isocenter of the LINAC. As described for FIG. 1, a particular target position with reference to the reference frame 1 which may be established in a stereotactic position relative to 1 and thereby be set up at isocenter 5 of the LINAC.

Also shown in FIG. 7 is an X-ray film 89 on the opposite side of reference frame one from the source S'. S' may be the source of X-rays, and a film projection of the X-ray beam can be shot onto the film 89 to give a port film shape represented by the line 90. A predetermined or calculated port shape 38 on reference box 1 may be contoured with a lead wire, and it may project as line 91 on port film 89.

Observing that contours 90 and 91 are in accordance with each other, or have a predicted relationship to each other, would indicate that the reference box 1 is properly aligned relative to the source S' and isocenter 5. Furthermore, a radiopaque marker 92 may be placed along the principal axis 17' to point 5, and its projection 93 may appear at a prescribed position on the port film to confirm that indeed point 91 is on the axis 17. Such methods and other variations are a quality assurance system for beam ports and the reference frame 1. The reference frame 1 may be attached to or connected to the patient's head, somewhat in similar arrangement as in FIG. 1. The patient may also have tattoos marked on his skin according to laser lines such as 17 to confirm that his bodily position is in the correct relationship to, say, the principal axis 17 and after alignment checks, therefore, in the correct relation to the reference frame 1. The entire reference frame can be placed in stereotactic relationship to the isocenter 5, as suggested in the above discussion. The ports 9, 86, and others may also be established to point at isocenter 5 on the LINAC and in predetermined or known directions corresponding to the LINAC couch and gantry angles. These light projections may then be use to determine the reference frame contours, as described in FIG. 7. Plus, the ports themselves may be used as a method for establishing the contours on the stereotactic reference frame 1 as an alternative to the method described previously, where the contours are established as a printout from the treatment planning computer system, for example. The reference box 1 may be of rectangular or cubicle form, as shown in FIG. 7, or it may be, for example, a cylindrical structure with rounded dome top. The surface may be frosted or sandblasted to better show the field light projections such as contour 21 or 84. It may be adapted to hold computer printouts from a treatment planning program. It may be adapted to be marked upon by a pen, for example, so that upon casting a field light, shown in FIG. 7, a technologist can simply trace the port contour onto the surface of frame 1. Frame 1 may have docking or anchoring means to the LINAC couch 4, or it may be fixed to the patient itself by, for example, a head ring, body cast, dental tray, ear bars, or other reference structure to the patient's anatomy. Thereby, frame 1 can be established relative to the patient's anatomy or relative to the LINAC ouch, as may be desired. Establishing it relative to the patient's anatomy is analogous to the stereotactic method of the XKnife Radiosurgery System, where invasively fixed or non-invasively relocatably fixed frames are used. This, then, references the reference frame to image scan data of the patient's body, that data in some cases being established relative to a graphic reference device such as a CT localizer, fiducial markers placed on the skin, or other such structures.

I claim:

1. A beam referencing system for radiation therapy equipment comprising:
   a collimator having an aperture to define a radiation beam from a radiation therapy source to irradiate a patient's body from a direction;
   A reference structure positioned in a known position with respect to said patient's body and comprising a beam contour representative of the projection of said radiation beam through said aperture from said direction.

2. The system according to claim 1 wherein said radiation therapy source comprises a light source to project light through said aperture along said direction so that said light will cast a light contour of said aperture onto said reference structure, whereby said light contour and said beam contour can be visually compared.

3. The system according to claim 1 wherein said reference structure comprises a patient localizer to position said patient's body with respect to said radiation beam and a beam reference structure with a projection surface that includes said beam contour.

4. The system according to claim 3 wherein said beam reference structure includes a plastic frame which can be attached in a fixed position with respect to said patient's body.

5. The system according to claim 1 wherein said reference structure comprises a target index representative of the position of a target in said patient's body with respect to said radiation therapy source.

6. The system of claim 3 wherein said patient localizer includes a target index representative of the position of a target in said patient's body with respect to said radiation therapy source.

7. The system according to claim 1 wherein said beam contour is derived from the output of a treatment planning computer.

8. The system according to claim 1 wherein said beam contour is derived from a light ray projection through said aperture onto said reference structure when said collimator is positioned according to said direction.

9. The system according to claim 1 wherein said radiation therapy system is a LINAC and said direction is in accordance with the LINAC gantry and couch angles.

10. The apparatus according to claim 7 wherein said beam contour is a printout onto a beam target sheet that couples to said reference structure.

* * * * *